United States Patent
Wang

[11] Patent Number: 5,865,034
[45] Date of Patent: Feb. 2, 1999

[54] METHOD AND APPARATUS FOR MEASURING ICE AMOUNT OF ICE TANK FOR ICE-STORAGE TYPE AIR-CONDITIONING SYSTEM

[75] Inventor: Michael Wang, Taipei, Taiwan

[73] Assignee: Yuan Ding Construction Co., Ltd., Taipei, Taiwan

[21] Appl. No.: 876,707

[22] Filed: Jun. 16, 1997

[51] Int. Cl.[6] .......................................... F25C 1/00
[52] U.S. Cl. ................................... 62/139; 62/201
[58] Field of Search .............................. 62/137, 138, 139, 62/140, 59, 201, 129, 130; 340/580

[56] References Cited

U.S. PATENT DOCUMENTS

| | | | |
|---|---|---|---|
| 3,496,733 | 2/1970 | Parker et al. | 62/139 |
| 3,502,899 | 3/1970 | Jones | 62/139 X |
| 4,823,556 | 4/1989 | Chesnut | 62/201 X |
| 4,843,830 | 7/1989 | Haul | 62/139 X |
| 5,163,298 | 11/1992 | Hassell et al. | 62/59 |
| 5,761,920 | 6/1998 | Wilson et al. | 62/138 |

*Primary Examiner*—Harry B. Tanner
*Attorney, Agent, or Firm*—Rosenberg, Klein & Bilker

[57] ABSTRACT

An apparatus for measuring ice amount of ice tank for ice-storage type air-conditioning system generally includes an operation control circuit and a software control flow for the operation control circuit, characterized in that the amount of ice in the ice tank is precisely calculated from the conductivity of the water in the ice tank through the operation control circuit as input data for energy management control system to improve the efficiency for the air-conditioning system.

2 Claims, 6 Drawing Sheets

METHOD AND APPARATUS FOR MEASURING ICE AMOUNT OF ICE TANK FOR ICE-STORAGE TYPE AIR-CONDITIONING SYSTEM

BACKGROUND OF THE INVENTION

1. Field of the Invention

This invention is related to a method and apparatus for measuring ice amount of ice tank for ice-storage type air-conditioning system and in particular to one by which the amount of ice in the ice tank can be precisely calculated from the conductivity of the water in the ice tank as input data for energy management control system to improve the efficiency for the air-conditioning system.

2. Description of the Prior Art

There are two major types of ice making machine: ice-on coil type and dynamic harvest type. Conventional ice storage HVAC systems are ice-on coil type which uses a coil in ice tank to make ice. During ice producing process, ice is attached on the surface of the coil and the water level in ice tank is slightly increased with the amount of ice made. A liquid level sensor is employed as the ice inventory sensor for the coil-type ice maker.

Modern ice storage systems are dynamic type ice harvester. Ice water is pumped from the ice storage tank and distributed to a thin film surface of ice making plate in ice harvester above the ice tank and returned to the ice storage tank by gravity. When water temperature is low, some of the water is frozen into sheets of ice. Periodically, hot gas is injecting into ice making plate to melt a thin layer of ice slab. Ice is then released from ice harvester and dropped into ice tank.

The liquid level sensor for the conventional coil-type ice maker is not an adequate instrument to measure the amount of ice for dynamic ice harvester. The density of ice is 0.92. Hence, before all the water in ice tank is becoming ice, the ice slab or ice particle is floated on the water surface. The volume of ice underneath the water surface and the volume of water transformed into ice are equal. Water level will not change until ice has reached the bottom of the ice tank, and the liquid level sensor will not be able to distinguish half tank of ice from no ice.

So far, there is no adequate method to correctly measure the amount of ice in the ice tank for dynamic type ice harvest systems. The ice inventory in ice tank is an essentially important parameter for effective control of thermal storage management for large scaled HVAC industries.

Therefore, it is an object of the present invention to provide a method and apparatus for measuring ice amount of ice tank for ice-storage type air-conditioning system by which the amount of ice in the ice tank can be precisely calculated from the conductivity of the water in the ice tank as input data for energy management control system to improve the efficiency for the air-conditioning system.

SUMMARY OF THE INVENTION

This invention is related to a method and apparatus for measuring and controlling ice amount of ice tank for ice-storage type air-conditioning system.

It is the primary object of the present invention to provide a method and apparatus for measuring ice amount of ice tank for ice-storage type air-conditioning system and in particular to one by which the amount of ice in the ice tank can be precisely calculated from the conductivity of the water in the ice tank as input data for energy management control system to improve the efficiency for the air-conditioning system.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numberals refer to identical or similar parts.

DETAILED DESCRIPTION OF THE PREFERRED EMBODIMENT

Figure 1:
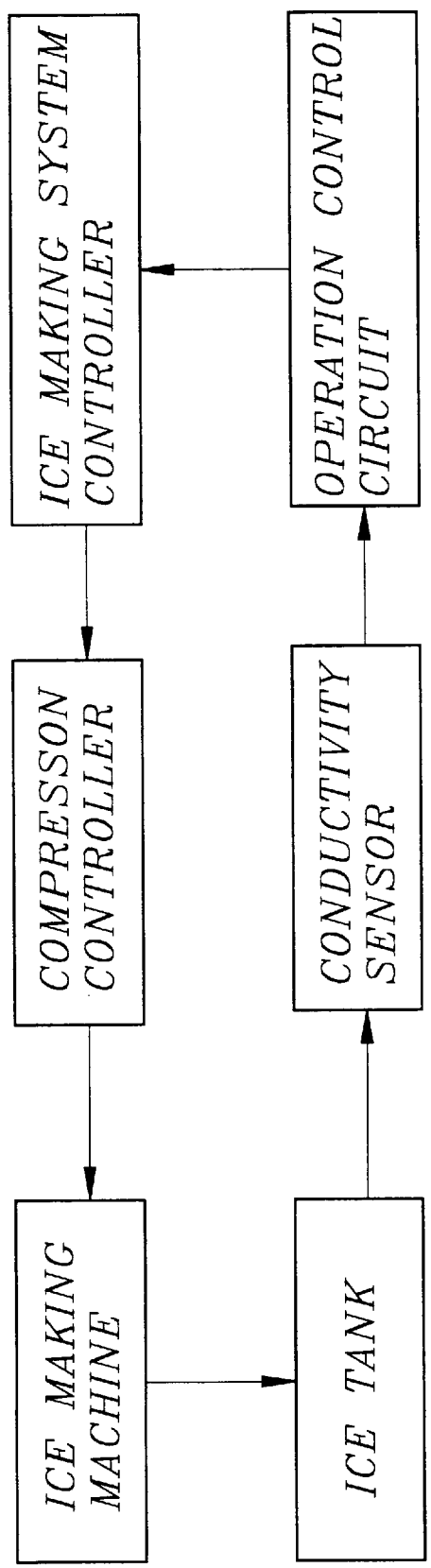
FIG. 1 illustrates the relationship between an ice-storage type air-conditioning system and the present invention.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

The method of measuring ice amount of ice tank for ice-storage type air-conditioning system generally comprises an operation control circuit and a software control flow therefor.

FIG. 1 illustrates the relationship between the operation control circuit and an ice-storage type air-conditioning system. After ice water is converted into ice blocks by an ice-making device, the ice blocks will drop into an ice tank. The conductivity of the ice water is measured by an external conductivity sensor and used as an input parameter for the operation control circuit. The parameter is compared by a comparator and converted into ice amount in the ice tank which is provided for the ice making system controller so as to determine the output power of the compressor controller and the time for switching on or off the compressor.

Figure 2:
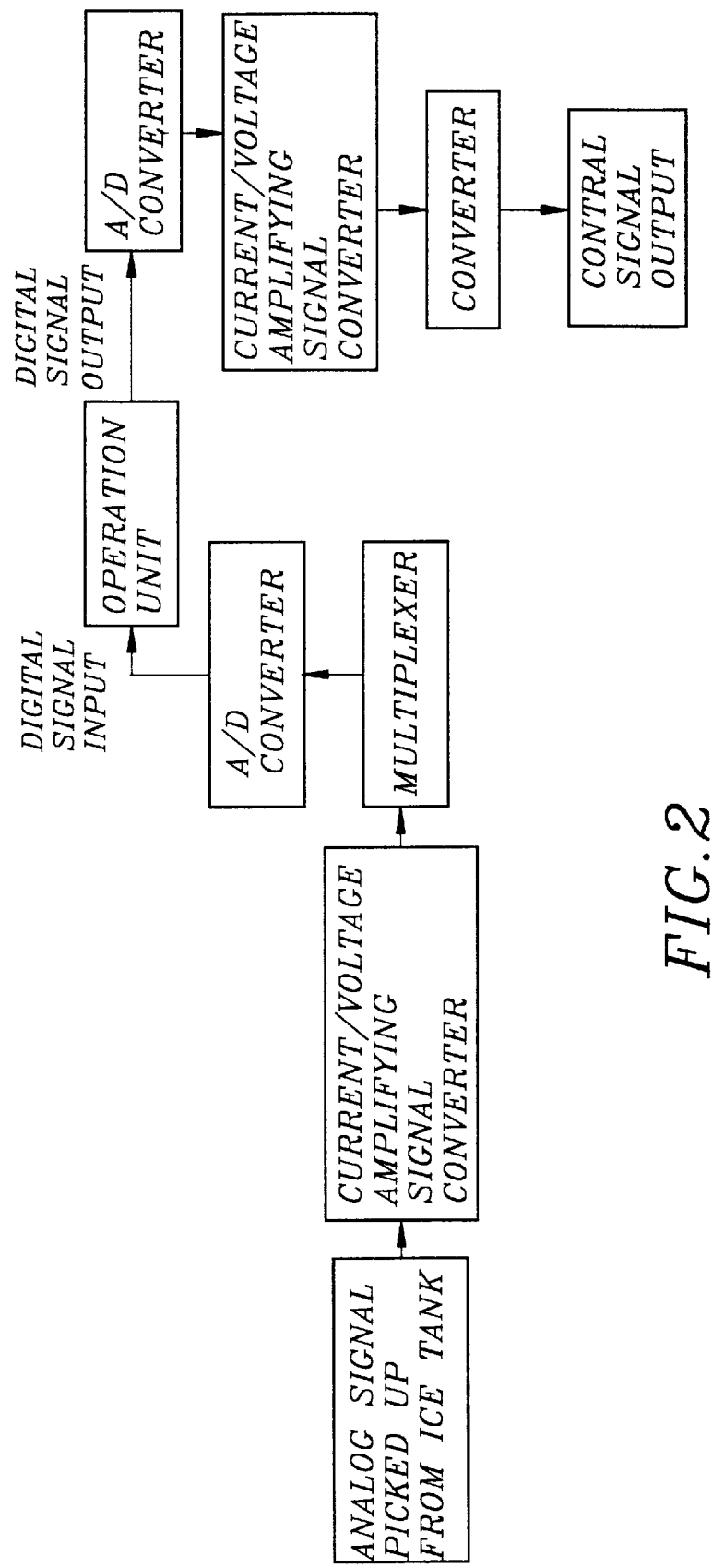
FIG. 2 is a block diagram of the operation control circuit.
Figure 3:
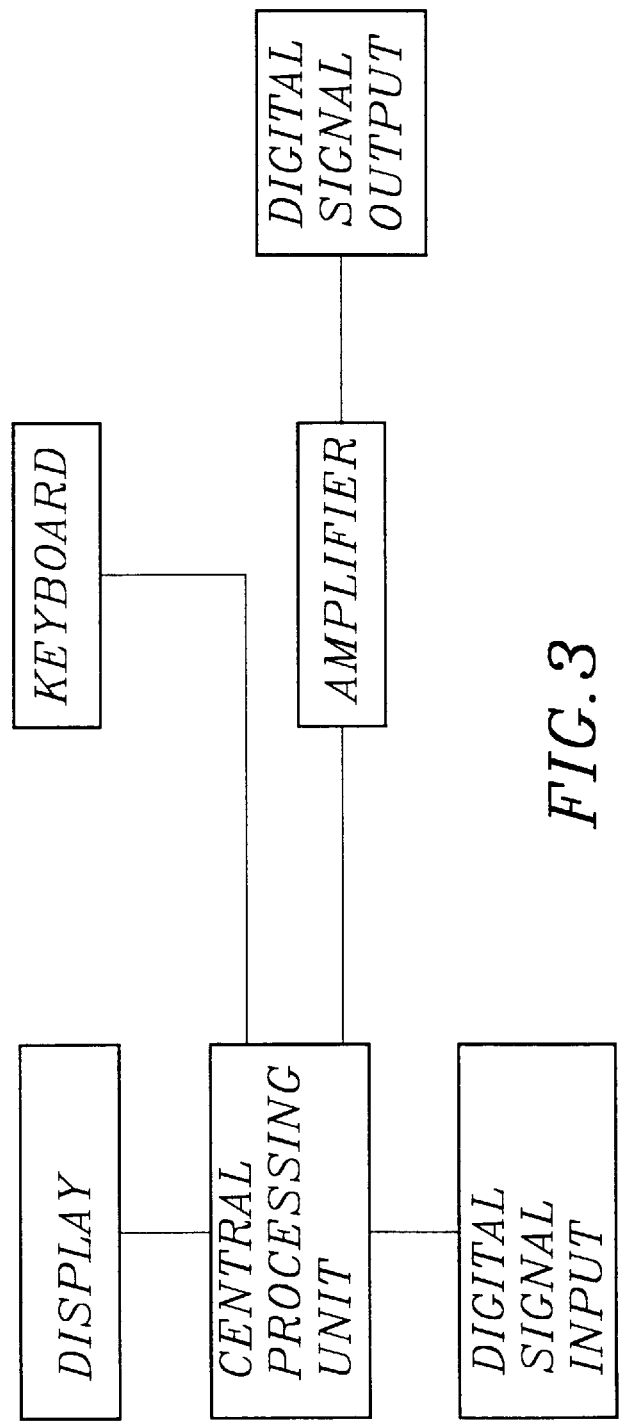
FIG. 3 is a block diagram of the operation unit.

FIGS. 2 and 3 illustrate the block diagrams of the operation control circuit and the operation unit respectively. The operation control circuit generally comprises an analog-to-digital signal converter, an operation unit and a digital-to-analog signal converter.

Figure 4:
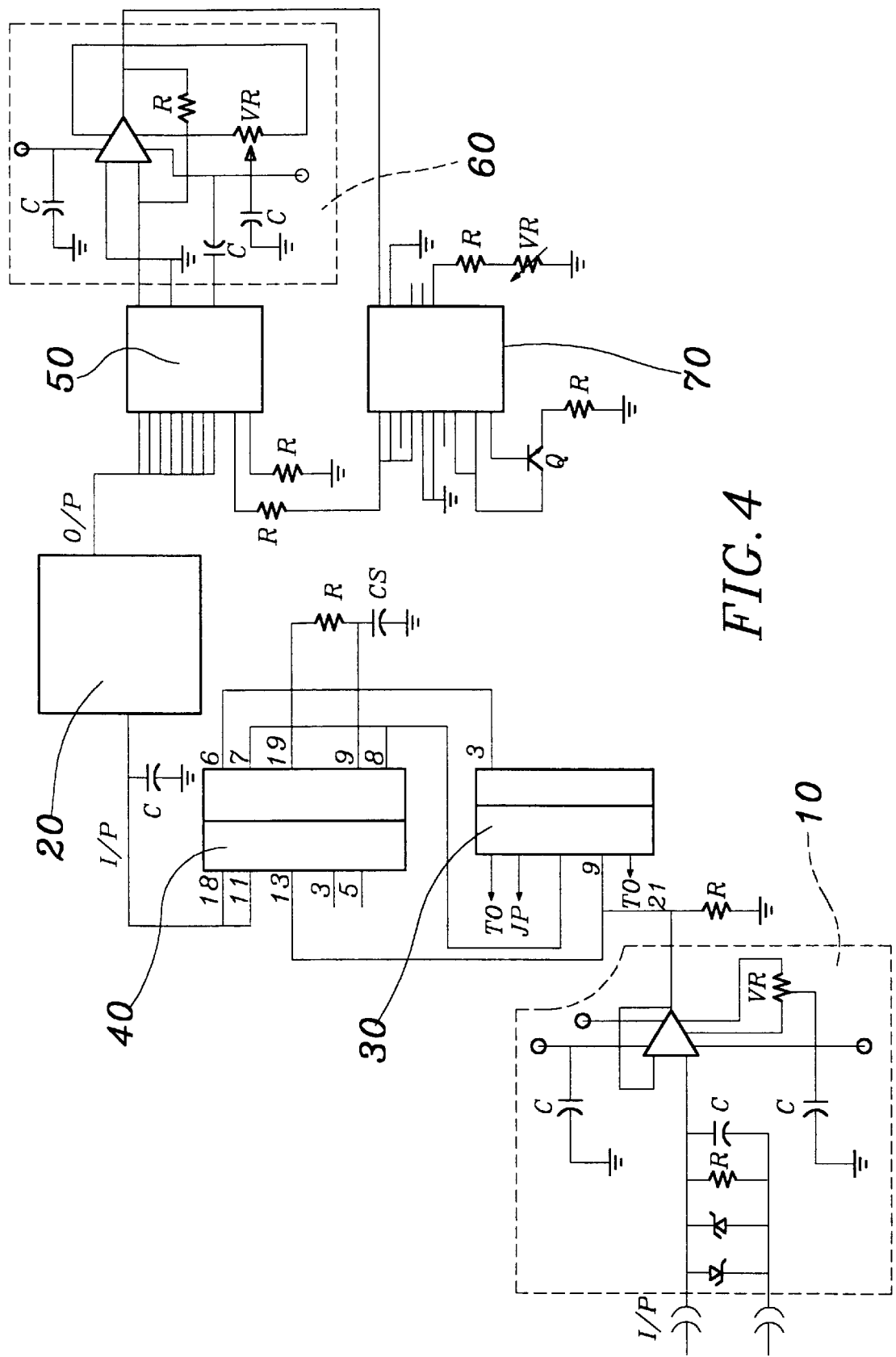
FIG. 4 is a circuit diagram of the operation control circuit.

FIG. 4 illustates a circuit diagram of the operation control circuit. As shown, an analog signal of 4–20 $\mu$ ampere picked up from the ice tank by an external conductivity sensor is first input into a current-to-voltage amplifying signal converter 10 which turns the analog signal into a standard analog signal with 1–5 volts. Then, the standard analog signal is converted into digital signal by a multiplexer 30 and an analog-to-digital converter 40 and sent to the operation unit 20 for operation processing.

Figure 5:
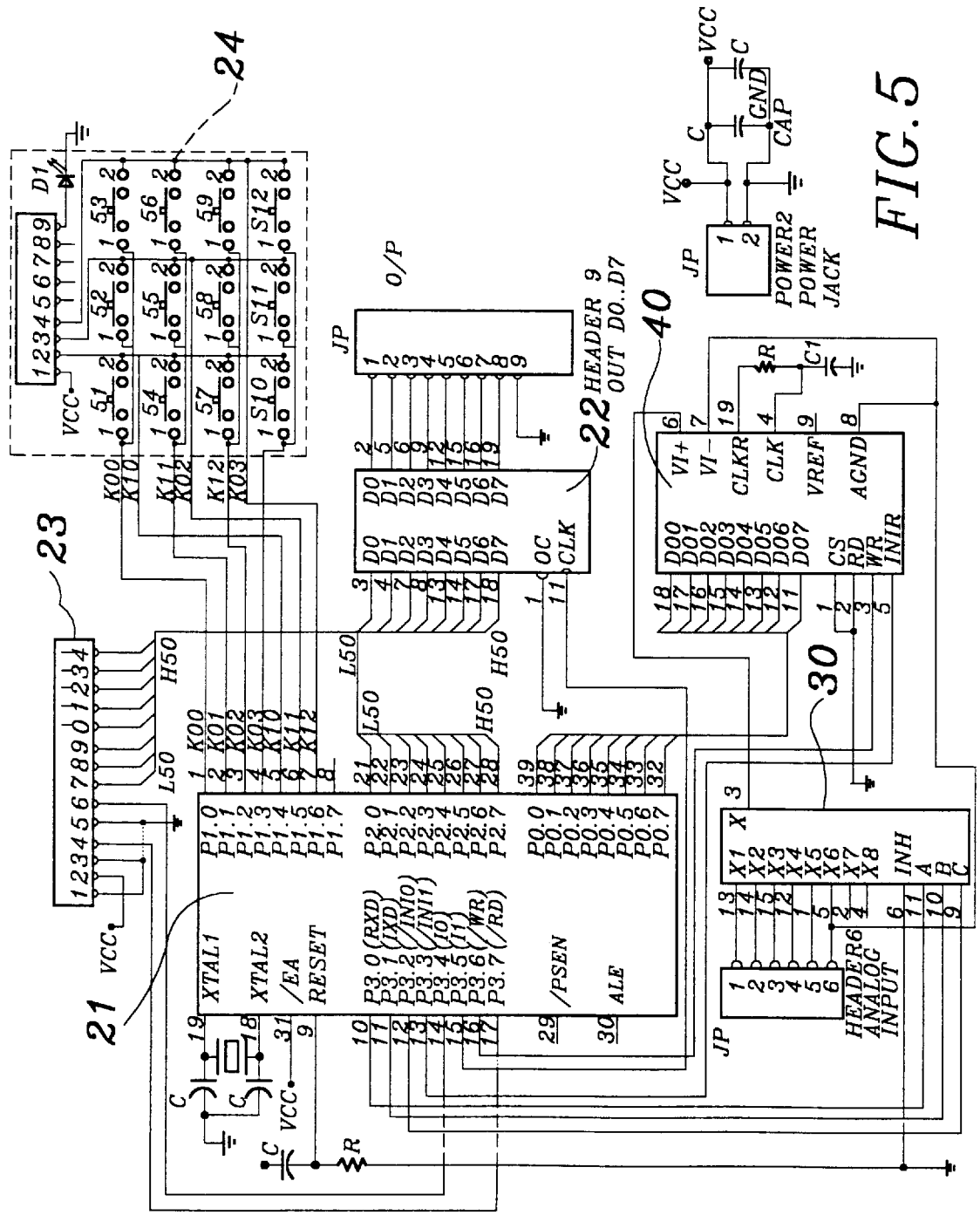
FIG. 5 is a circuit diagram of the operation unit.

FIG. 5 is a circuit diagram of the operation unit. As shown, the signal input into the operation unit is first calculated, analyzed and compared by the operation unit and then the signal is sent to the central processing unit 21 for data operation processing by means of the software control flow therein. In addition to the data input by an operator through a keyboard 24, the operation result will be shown in a LCD display 23 for providing the operator to monitor the conditions and decide what has to be done. Furthermore, the weak digital signal resulted from the operation will be enlarged by an amplifier 22 to be controllable standard digital signal which will then be sent out of the the operation unit.

Referring to FIG. 4 again, the digital signal out of the operation unit is finally converted by a digital-to-analog converter 50, current-to-voltage amplifying signal converter 60 and converter 70 into a standard digital control signal with 4–10 $\mu$ ampere and 2–10 volts for providing a control parameter for the ice-storage type air-conditioning system thereby achieving the purpose of accurately controlling the ice making rate.

Figure 6:
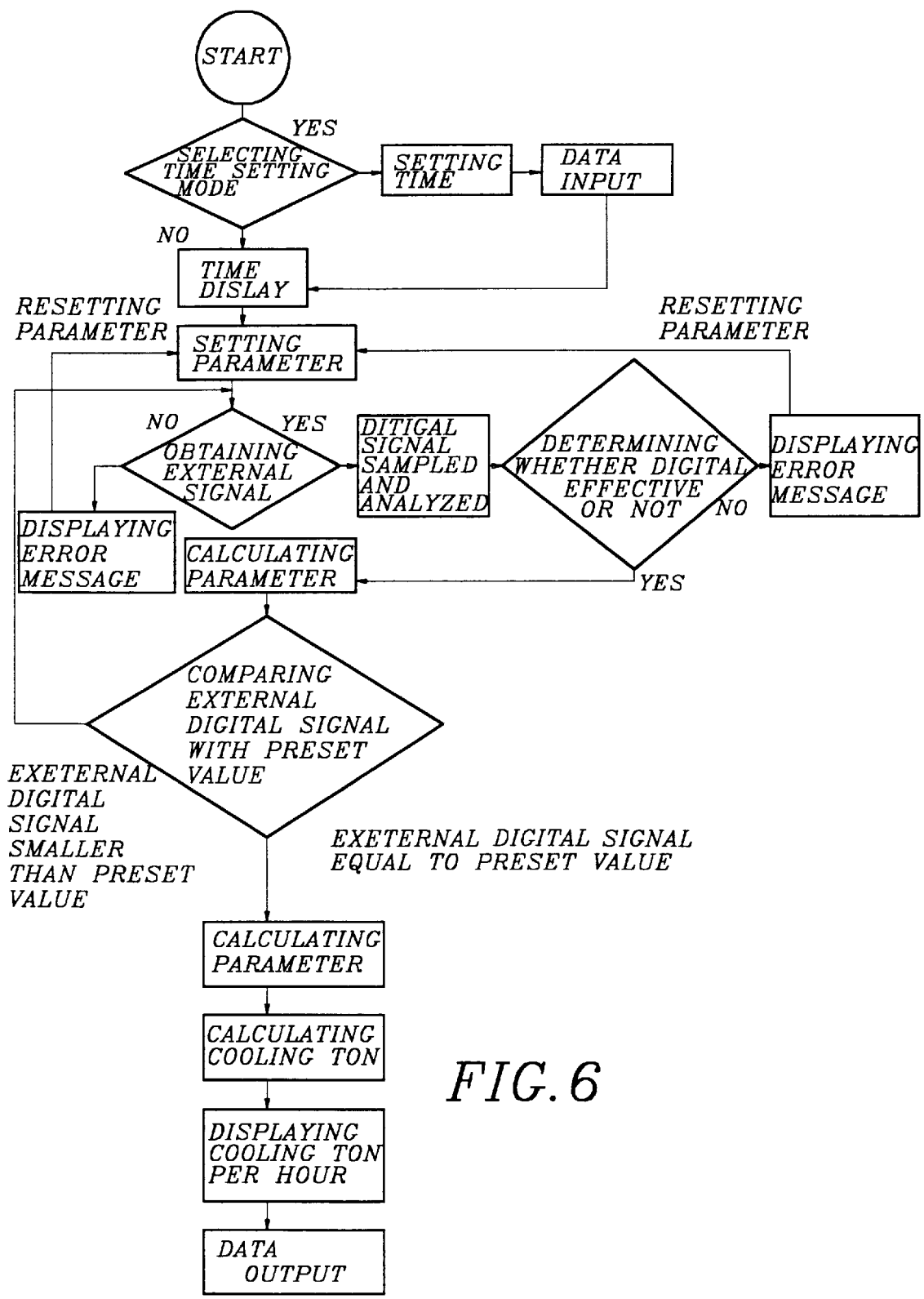
FIG. 6 illustrates the software control flow chart according to the present invention.

FIG. 6 is the software control flow chart according to the present invention. The software control flow chart generally comprises signal and data input, operation, and signal and data output.

As the program starts, the time mode is first selected by inputting the time through a keyboard to show the set time in a display and then the initial parameters (initial conductivity and correction coefficient) are input by the keyboard for providing a comparative standard for the running of the program.

The operation unit picks up conductivity digital signal obtained from the ice tank by the conductivity sensor via a delay circuit. If the signal picked up is negative, the display will show an error message and request resetting parameters. If the signal picked up is positive, the digital signal will be sampled and analyzed by the program operation of the operation unit to determine whether this signal is effective or not. If the result is negative, the display will show an error message and request resetting the parameter. If the result is positive, the parameter will be calculated and compared with the initial value. If the digital signal picked up from the exterior is smaller than the preset value, its means that the ice amount does not reach the preset level and the program will request a new external digital signal for comparison until the external signal is larger or equal to the preset valve. That is, when the ice amount reaches the preset ice amount, the operation unit will calculate the parameter and the cooling capability accordingly.

Finally, the cooling ton per hour will be shown in the display and digital data will be given to provide a reference for the decision of ice making rate for the ice making system.

Accordingly, the method and apparatus for measuring ice amount of ice tank for ice-storage type air-conditioning system according to the present invention can be used for precisely calculating the amount of ice in the ice tank from the conductivity of the water in the ice tank so as to provide input data for energy management control system to improve the efficiency for the air-conditioning system.

This invention is related to a method and apparatus for measuring ice amount of ice tank for ice-storage type air-conditioning system and in particular to one by which the amount of ice in the ice tank can be precisely calculated from the conductivity of the water in the ice tank as input data for energy management control system to improve the efficiency for the air-conditioning system.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. An apparatus for measuring ice amount of ice tank for ice-storage type air-conditioning system comprising:

an operation control circuit and software control flow for said operation control circuit, said operation control circuit including an analog-to-digital signal converter, an operation unit and an digital-to-analog signal converter;

a sensor for picking up analog signal from said ice tank;

whereby when said sensor picks up an analog signal from said ice tank, said analog signal is converted into digital signal by said analog-to-digital signal converter, said digital signal being calculated and analyzed by said operation unit and sent out of said operation unit to be converted by said digital-to-analog signal converter into analog control signal for providing control parameter for an automatic control system;

a software control flow wherein initial parameter is input through a keyboard when a program starts so as to provide a comparing basis for signal obtained during running of said program;

said operation unit picking up conductivity digital signal from said ice tank by means of said sensor via a delay circuit: if said signal picked up is negative, a display will show an error message and request resetting parameters, and if the signal picked up is positive, the digital signal will be sampled and analysed by said program of said operation unit to determine whether said signal is effective or not, and if result is negative, said display will show an error message and request resetting the parameter, and if said result is positive, parameter will be calculated and compared with said initial value;

if said digital signal picked up from exterior is smaller than preset value, ice amount does not reach said preset level and said program will request a new external digital signal for comparison until external signal is larger or equal to said preset value so that when said ice amount reaches preset ice amount, said operation unit will calculate out parameter and cooling capability and send out digital data to provide a reference for decision of ice making rate for ice making system.

2. The apparatus for measuring ice amount of ice tank for ice-storage type air-conditioning system as claimed in claim 1, wherein said operation control circuit comprises: an external conductivity sensor for picking up analog signal from an ice tank; a current-to-voltage amplifying signal converter for converting said analog signal into standard analog signal; a multiplexer and an analog-to-digital converter for converting said standard analog signal into digital signal; and an operation unit for processing said digital signal;

whereby when said operation unit receives said digital signals, said digital signal will be sent to a central processing unit for data operation processing by means of operation of said software control flow and in association with data keyed in by an user, and operation processing result will be shown in a display and will be enlarged by an amplifier into controllable standard digital signal which will be sent out of said operation unit via a digital signal output terminal, said digital signal being converted through a digital-to-analog converter and current-to-voltage amplifying signal converter and a converter into standard analog control signal as control parameter for an ice-making system for an ice-storage type air-conditioning system.

* * * * *